United States Patent
Zachrisson

(10) Patent No.: US 6,681,423 B2
(45) Date of Patent: Jan. 27, 2004

(54) SURGICAL TABLE WITH DISPLACEMENT ARRANGEMENT

(75) Inventor: Bjorn Zachrisson, Sollentuna (SE)

(73) Assignee: Stille Surgical AB, Stockholm (SE)

( * ) Notice: Subject to any disclaimer, the term of this patent is extended or adjusted under 35 U.S.C. 154(b) by 0 days.

(21) Appl. No.: 10/239,196

(22) PCT Filed: Mar. 29, 2001

(86) PCT No.: PCT/SE01/00687

§ 371 (c)(1), (2), (4) Date: Sep. 27, 2002

(87) PCT Pub. No.: WO01/72226

PCT Pub. Date: Oct. 4, 2001

(65) Prior Publication Data

US 2003/0074735 A1 Apr. 24, 2003

(30) Foreign Application Priority Data

Mar. 29, 2000 (SE) .............................. 0001117

(51) Int. Cl.⁷ ............................ A61B 6/04; A61G 13/04
(52) U.S. Cl. ................................... 5/610; 5/601; 5/608
(58) Field of Search ............................ 5/607, 608, 601, 5/600, 610

(56) References Cited

U.S. PATENT DOCUMENTS

| | | | | |
|---|---|---|---|---|
| 4,761,000 A | | 8/1988 | Fisher et al. ................ 269/323 |
| 5,230,112 A | * | 7/1993 | Harrawood et al. ........... 5/608 |
| 5,490,297 A | | 2/1996 | Bradcovich .................... 5/601 |
| 5,590,429 A | | 1/1997 | Boomgaarden et al. ........ 5/600 |
| 5,774,915 A | * | 7/1998 | Scott et al. .................... 5/610 |
| 6,560,799 B1 | * | 5/2003 | Pflaum et al. ................. 5/600 |
| 6,574,808 B1 | * | 6/2003 | Brown et al. .................. 5/601 |

FOREIGN PATENT DOCUMENTS

| | | |
|---|---|---|
| DE | 1219625 | 9/1964 |
| DE | 2803312 | 8/1979 |
| EP | 0457248 A2 | 11/1991 |
| EP | 0923922 A2 | 6/1999 |
| FR | 2749503 | 12/1997 |
| JP | 11313900 | 11/1999 |

* cited by examiner

Primary Examiner—Frederick L. Lagman
(74) Attorney, Agent, or Firm—Jacobson Holman PLLC

(57) ABSTRACT

A surgical table (1) comprises a longitudinal, at least partly radiolucent table top (2), a support structure (3) for the table top, said support structure including a lateral tilting mechanism (4) for providing lateral tilting movement to the table top (2), a base (B) for supporting the support structure and the table top, and lateral floating means (6) for allowing the table top a floating horizontal movement in lateral directions relative to the base (5). According to the invention said lateral floating means (6) are positioned below the lateral tilting mechanism (4) for permitting undisturbed lateral floating movement in horizontal as well as tilted positions of the table top (2).

19 Claims, 7 Drawing Sheets

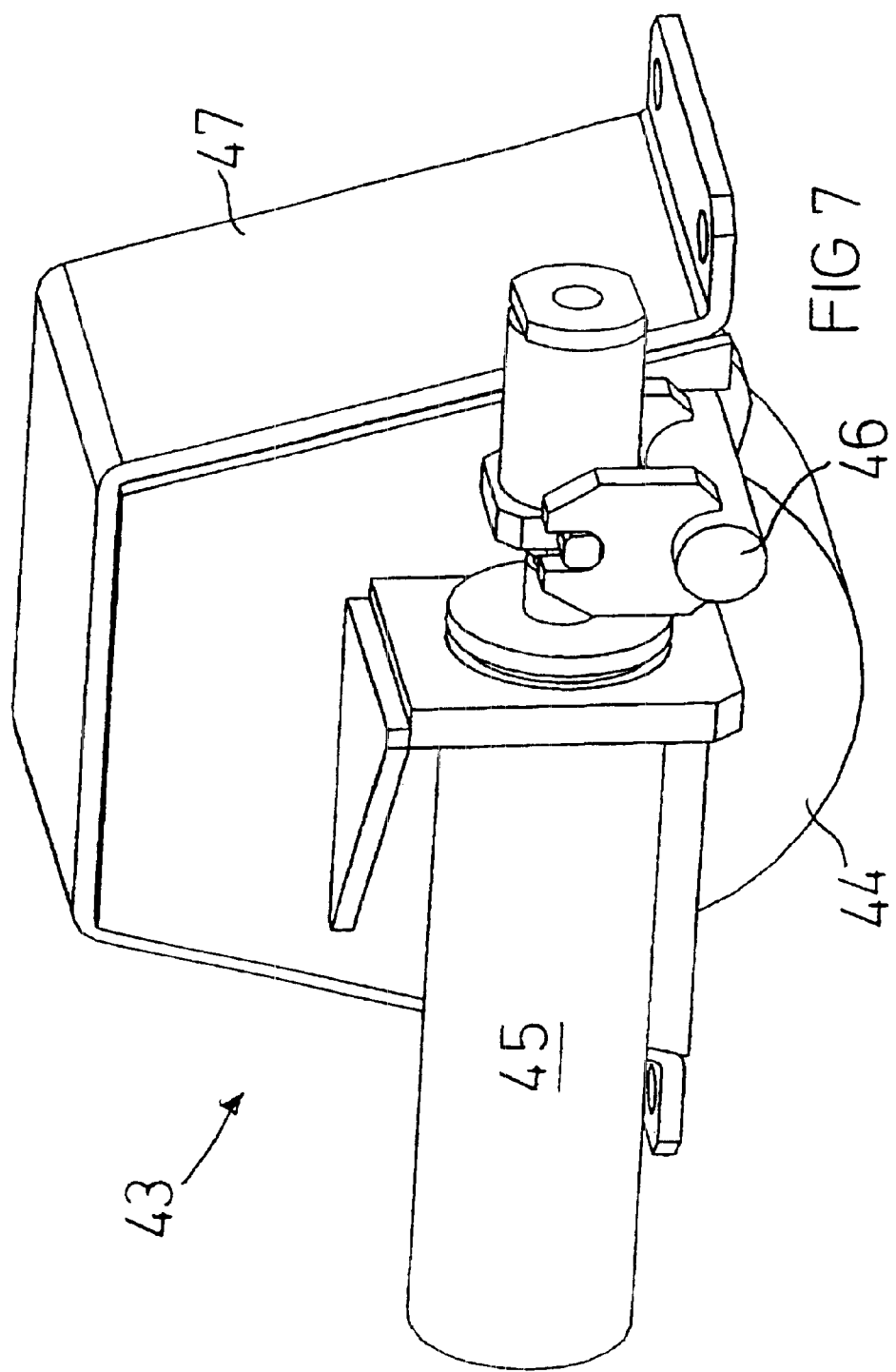

SURGICAL TABLE WITH DISPLACEMENT ARRANGEMENT

This is a nationalization of PCT/SE01/00687 filed Mar. 29, 2001 and published in English.

FIELD OF THE INVENTION

This invention concerns a surgical table according to the preamble of claim 1.

DESCRIPTION OF PRIOR ART

Surgical tables of today provide movements in various dimensions such as elevation of the table and tilting about the longitudinal as well as the transversal axis. These various movements are desirable for adoption to particular operating situations and also, in case of a surgical table having a radiolucent table top, i.a. for allowing freer X-ray imaging of a particular body part. In particular, lateral tilt is used for allowing organs to be imaged from different directions as desired and in some cases for displacing "loose" organs from each other or from "fixed" organs in order to obtain improved images.

EP-A2-0 923 922 concerns an operating table for surgical as well as imaging procedures. The table comprises a radiolucent table top and means for providing the table top with vertical lift, longitudinal tilt, lateral tilt and a four-way floating movement. A control switch is provided which is effective to permit floating movement of the table top along a horizontal axis and ineffective to permit floating movement along a tilted axis. The table top is thereby totally prevented from floating movement when tilted both longitudinally and laterally, it is free to float laterally, but not longitudinally when tilted only longitudinally, and it is free to float longitudinally but not laterally when tilted only laterally. When the table top is horizontal it is free to float in either direction.

According to EP-A2-0 923 922, lateral movement of the table top is thus not permitted when the table top is subjected to a lateral tilt and the reason for this is that when being laterally tilted there is a risk of the table top falling down to the lowermost position. Given that adult patients often weigh well over 100 kg, free movability in lateral directions could be dangerous for the patient as well as for the personnel, since it could jeopardise the stability of the entire table. The provision of automatic lock is therefore to be regarded as an important safety measure according to this EP document.

When examining a patient using imaging equipment, the table top is usually floated with respect to the fixed imaging equipment in order to obtain the best images of the organ to be examined. In the prior art device according to EP-A2-0 923 922, however, it is difficult for the surgeon to freely and flexibly scan the area around the organ of the patient to be examined in a lateral tilted position of the table top. In real time imaging as well as in X-ray photography the surgeon can only use the floating movement in the horizontal position of the table top, when freely locating and examining the patient. This is thus only possible before tilting the table top.

If free adjustment is desired or necessary after reaching a tilted position, the surgeon will either have to try to adjust the tilt or to adjust the position of the imaging equipment, which is typically arranged on a so called C-arm, partly enclosing the table top and the part of the patient to be imaged. This is, however difficult and results in inexact positioning. This limitation with respect to the possibilities of obtaining an overview of the patient's organs as well as fine adjustment and flexibility has proved to be a serious drawback of the prior art.

OBJECT AND SUMMARY OF THE FEATURES OF THE INVENTION

It is an object of the invention to overcome the drawbacks of the prior art and to provide a surgical table, which allows greater flexibility with respect to handling and applicability. This object is attained with a surgical table according to the above through the features of the characterising portion of claim 1.

These features make it possible to achieve lateral movement in lateral directions of the table top also when the table top is subjected to a lateral tilt. This is possible because the lateral floating means are positioned so that they are unaffected by the lateral tilt. No particular power actuators are necessary for lateral movement even in lateral tilted positions of the table top since the lateral movement is unaffected by gravity forces. It should however be mentioned that the invention does not exclude using power assisted float.

As to the inventive surgical table, the table with the table top in all positions defines longitudinal directions along its longitudinal extension and lateral directions perpendicular thereto. The lateral tilting mechanism provides lateral tilting movement to the table top in parallel with the lateral directions. The lateral floating means is arranged such that it allows the table top floating horizontal movement in said lateral directions.

The invention brings along several advantages such as flexibility for the surgeon, increased accuracy and possibility of quicker diagnosis, which could be crucial with respect to the well-being of the patient and the success of the surgeon's efforts. No movement of the entire surgical table is necessary and no fine adjustment of the image C-arm.

It should be noted that lateral movability in lateral tilted positions of the table top takes care of most imaging and operating situations. The table may or may not be arranged for allowing longitudinal movability when the table top is subject to longitudinal tilt, e.g. by power float means. Longitudinal tilt will, however, not influence the lateral movability. In most operating and imaging situations, however, the table top is not longitudinally tilted.

According to a preferred aspect of the invention, the lateral tilting actuators are comprised of linkage mechanisms, which are arranged so as to obtain lateral tilting movement of the table top about an axis or axes located above the table top. This gives a vertically compact solution and makes it possible to tilt the table top and the patient around a position close to the organ to be investigated.

It should be noted that tilting of the table top is important for several reasons. Longitudinal tilting around a transversal axis (Trendelenburg tilting) for example allows placing the head lower than the rest of the patient's body, which compensates for low blood pressure in case of trauma. As has been mentioned above, lateral tilting around a longitudinal axis allows imaging from chosen directions. It also relocates certain organs such as the bowls thereby freeing other organs for examination. The invention makes it possible to fine adjust imaging in transversally tilted positions of the body, whereby the diagnosis may be enhanced and made quicker.

The aspect where the lateral tilting actuators are attached to first and second frames guarantees the stability of the construction. The frames also make it possible for a vertical carrier beam belonging to the base structure to extend through the insides of the frames, whereby the elevation path of the table top may be extended in an advantageous way (see claim 14).

According to a further aspect, the lateral tilting actuators may be comprised of program controlled actuators. These actuators are preferably located between first and second frames thereby guaranteeing the stability of the construction.

According to one further aspect, the provision of one part of the lateral floating means on the first frame provides for a simple and robust construction.

BRIEF DESCRIPTION OF THE DRAWINGS

Further advantageous achievements are obtained from other aspects of the invention, which will come clear from the following description of embodiments with reference to the drawing, wherein:

FIG. 7 shows a directional wheel arrangement to be used with a table according to the invention.

DESCRIPTION OF EMBODIMENTS

Figure 1:
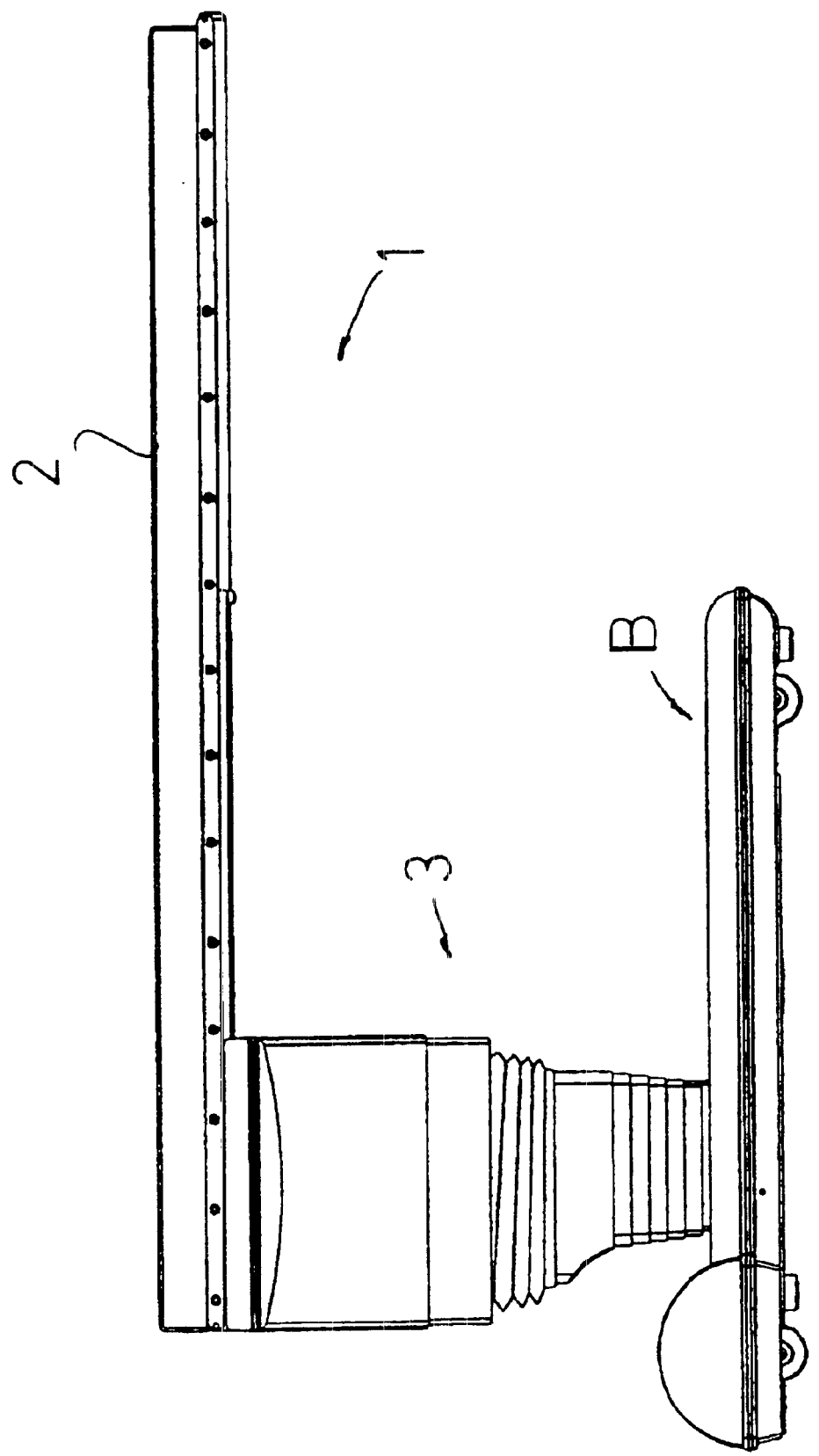
FIG. 1 shows in a side view a surgical table according to the invention but with protective hoods covering the movement mechanisms.

In FIG. 1 a surgical table 1 is shown having a table top 2 and a support structure 3 for providing the table top 2 with various movements.

Figure 2:
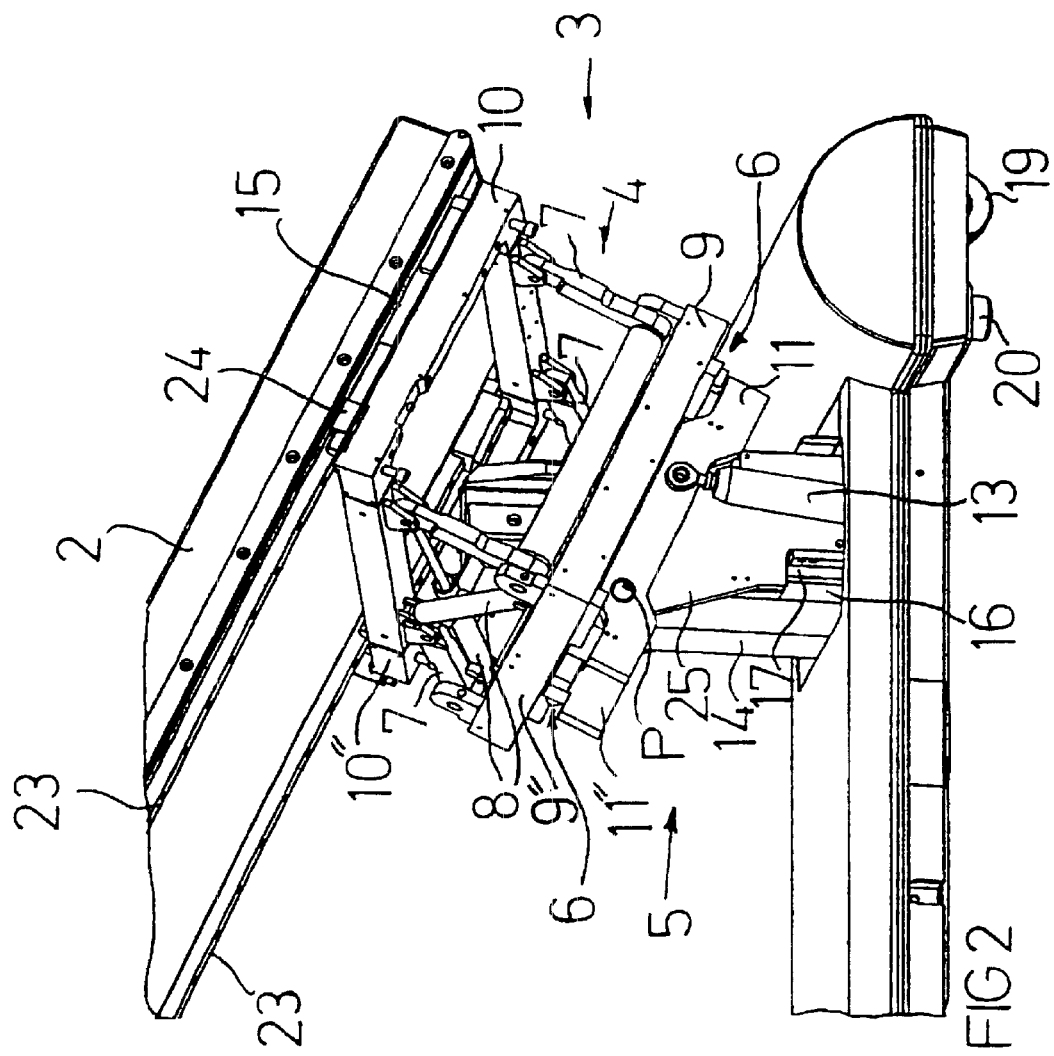
FIG. 2 shows in a perspective view the table of FIG. 1 dismantled.

The surgical table 1 is shown in FIG. 2 in a longitudinal as well as a lateral tilted position of the table top 2. The table top 2 is at least partially translucent and is carried by a support structure, in general indicated with 3. The support structure 3 includes a lateral tilting mechanism 4, a column unit 5 and elements for allowing a four-way float of the table top with respect to the column unit 5.

It is important, and it is to be noted, that the invention relates to a surgical table wherein the support structure and in particular the column unit 5 in all working positions are located generally inside a vertical area including the table top. This because of firstly stability reasons, since in use of the table stability is not jeopardised because heavy loads, such as from heavy patients, act directly vertically through the support structure and the column unit in the table according to the invention. Secondly for simplicity reasons, since the construction may be made straight forward, lightweight and uncomplicated because of advantageous load distribution and because of the fact that excess forces emanating from a heavy patient is avoided. Displacing the patient for imaging purposes may therefore be accomplished without instability being induced. Thirdly for accessibility reasons, since working on the table top is not obstructed in any position around the table because the support structure does not extend sideways in any direction to an extent worth mentioning from the vertical area including the table top.

The lateral tilting arrangement 4 includes two longitudinally separated linkage mechanisms each comprising a pair of links 7 which are positioned in planes essentially perpendicular to the table top 2 and to the longitudinal direction of the table top 2. The links are arranged so as to obtain a tilting movement of the table top 2 when actuating hydraulic cylinders 8. The cylinders 8 are arranged essentially diagonally within the linkage mechanism which is a four link mechanism consisting of the links 7 and transversal portions 9" and 10" of first 9 and second 10 frames which constitute the bottom part and the top part respectively of the lateral tilting arrangement.

The table top 2 is movable longitudinally with respect to the second frame 10 by means of a longitudinal floating arrangement 15 which is lockable so as to prevent unintentional movement of the table top.

A base B supports the surgical table 1 against the floor and is provided with castors (one shown at 19) so as to allow rolling movement of the table. The base B supports a vertical beam 16 having vertical guides 17 such as guide grooves and/or rails for guiding and supporting a vertically displaceable, partly sleeve shaped elevator member 25. At its top this elevator member 25 carries a support frame 11 which is pivotable with respect thereto, and in particular around a pivot axis P. The support frame 11 surrounds the beam 16 and co-operates at its top with the first frame 9 for lateral movement of the table top with respect to the column unit 5.

This is accomplished according to the shown embodiment by a lateral floating means 6 comprising elements allowing cooperation between the transversal elements 11" and 9" of the respective frames 9 and 11, so as to allow lateral movement of the first frame 9 with respect to the support frame 11. These lateral or "floating" movement elements also include locking members (not shown) so as to achieve fixation between these frames in desired positions.

The column unit 5 also carries a vertical lift actuator 14 in the form of a hydraulic twin cylinder, for providing a table top elevation. The vertical lift actuator 14 acts between a bottom portion (not shown) of the beam 16 and, at its top, the elevator member 25 at the support frame pivot axis P.

The column unit 5 also comprises longitudinal tilt actuators (only one shown) 13, which extend between the bottom of the elevator member 25 and a position on the support frame which is off-set the position P for attachment of the lift actuator 14. Actuation of the actuators 13 results in longitudinal tilt or Trendelenburg tilt of the support frame 11 and thereby of the table top 2.

The base B also comprises floor locks, one of which being indicated at 20. These locks are located at the right end on FIG. 2, which according to this aspect is defined as the column unit rear end 18. The floor locks are positioned behind the castor 19 as seen in a direction from the right to the left on FIG. 1. This arrangement gives free way from said direction to the castor 19, without risking that the floor locks block the movements of the surgical table 1 when it is for example rolled over an obstruction such as a door threshold. Also at the front end of the column unit the floor locks are positioned behind the castors, which can be best seen in FIG. 1.

Rails 23 at the bottom side of the table top 2 are provided for co-operation during longitudinal movements of the table top with guides 24 and (not shown) locks on top of the second frame 10.

Figure 3:
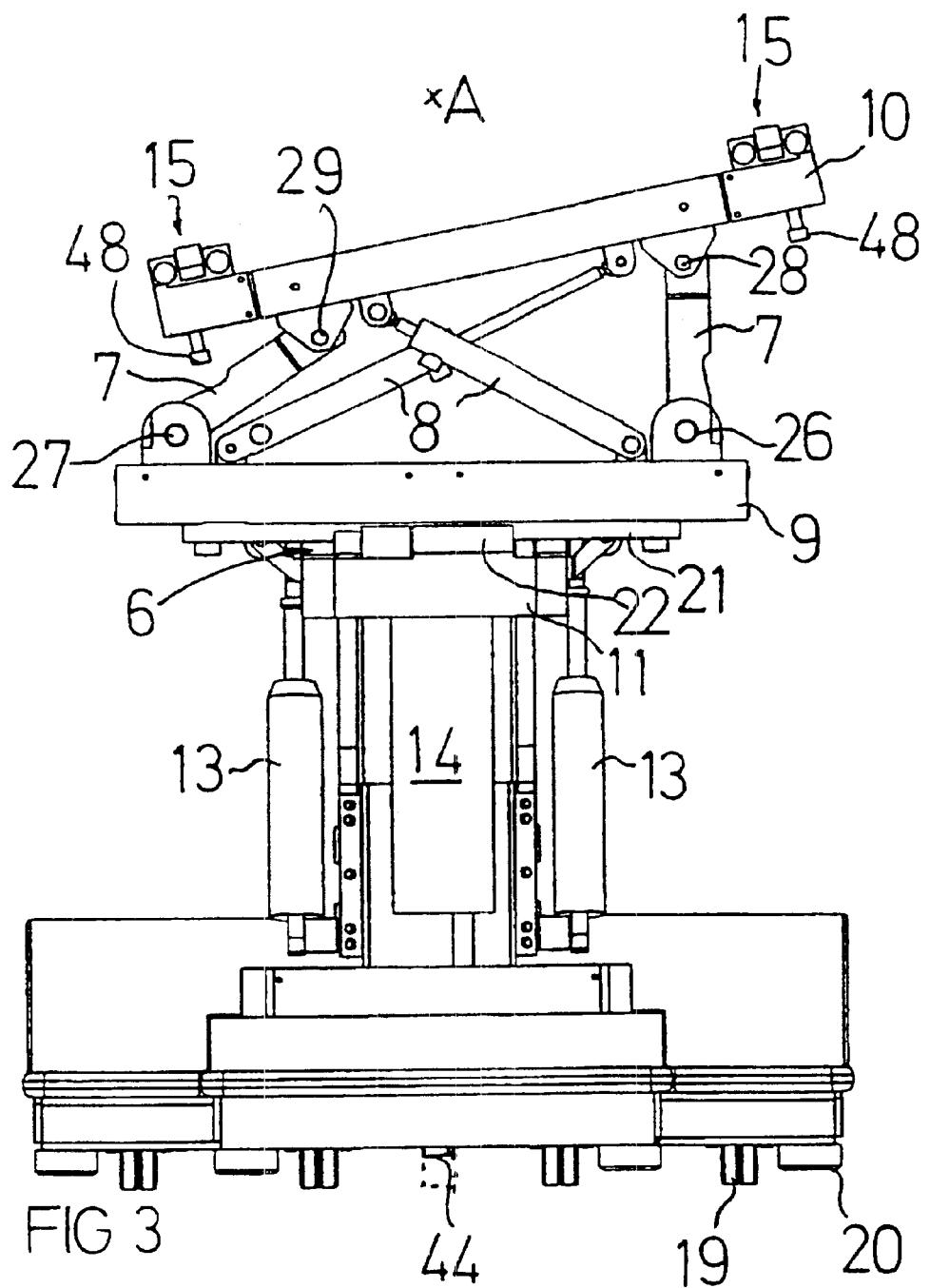
FIG. 3 shows a surgical table of FIG. 1 without the table top in an end view

In FIG. 3 the surgical table 1 is shown in an end view Trendelenburg tilted and laterally tilted so as to best illustrate the lateral tilting arrangement and the lateral floating elements but without the table top. As is clear from FIG. 3 the bottom ends of the links 7 are separated by a greater distance than the top ends of said links.

The relation between the lengths of the links, the distance between the bottom pivot points 26, 27 of the links 7 on the first frame 9 and the distance between the top pivot points 28, 29 of the links on the second frame 10 is calculated so as to obtain a four-link mechanism whereby a desired lateral tilting movement of the second frame and thereby the table top is achieved when tilting is initiated. The result in operation of this arrangement in that actuation of one of (or both) the two hydraulic cylinders 8 tilts the table top 2 in such a way that it appears to be tilted around an axis A (or a cluster of axes) being located above the table top.

It should be noted that the tilting movement is not necessarily a perfect rotational movement around one single axis A, and this is not important in this respect. It is however a great advantage to have the articulation of the table top around an axis or axes located above the table top since firstly this does not essentially displace the patient laterally when the table top is laterally tilted. Hereby excess forces on the equipment is avoided.

Secondly, neither does the tilting displace the organ to be examined essentially out of focus of an imaging device, which is typically used for real time imaging. Tilting laterally during simultaneous imaging can therefore be provided more easily.

Bolts 48 on the second frame 10 act as motion stops for preventing over-centre tilting of frame 11 with respect to frame 9.

Further from FIG. 3, at the bottom side of the first frame 9, rails 21 are arranged which co-operate for lateral movements of the table top with guides 22 and (not shown) locks at the top of the support frame 11. The locks being able to fix the lateral float in any desired position. According to the invention, the lateral float elements are constantly positioned horizontally, irrespective of the prevailing lateral tilt, because of the relative positioning of the devices with respect to each other. This makes it possible to use horizontal float in laterally tilted as well as in untilted positions.

Figure 4:
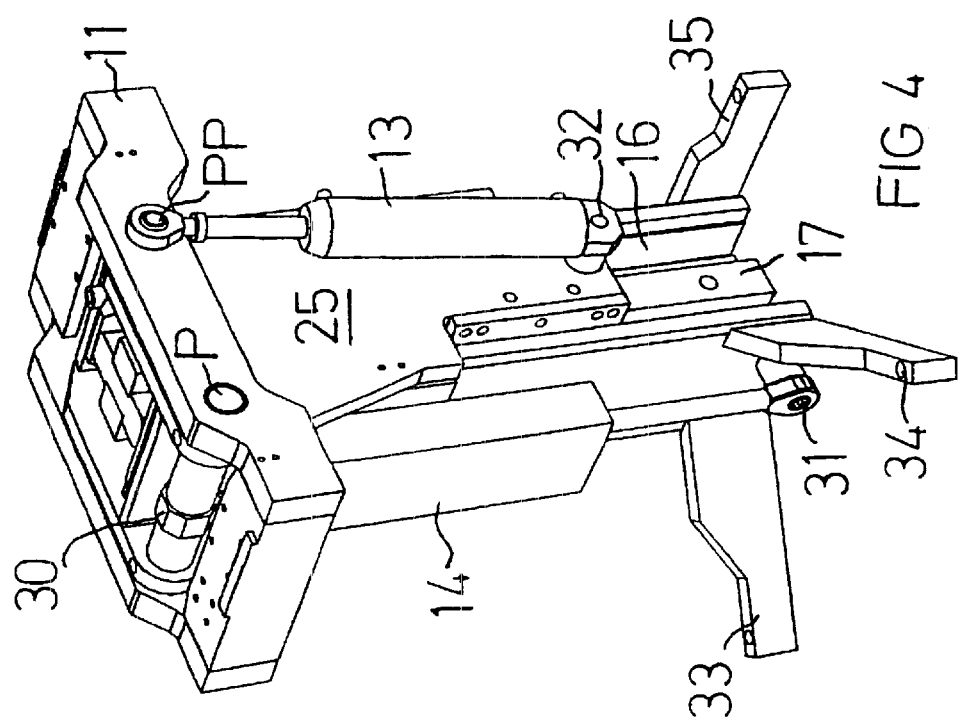
FIG. 4 shows, in a perspective view, the column unit of a table according to the invention.

FIG. 4 shows the column unit without the base. The vertical beam is at its bottom provided with an attachment arrangement 31 for the twin lift cylinder 14. 30 indicates the arrangement for fastening the cylinder 14 to the support frame pivot axis P. The twin cylinder arrangement simply consists of two cylinders which are fastened (or integrated) side by side with their respective pistons acting in opposite directions. Actuation of the twin cylinder 14 may be arranged such that both pistons extend before the other or such that one of the pistons make a full movement before the second piston starts to move. In any case, the twin cylinder arrangement provides for extended actuation length and reduced length in the retracted position of the cylinder.

Figure 5:
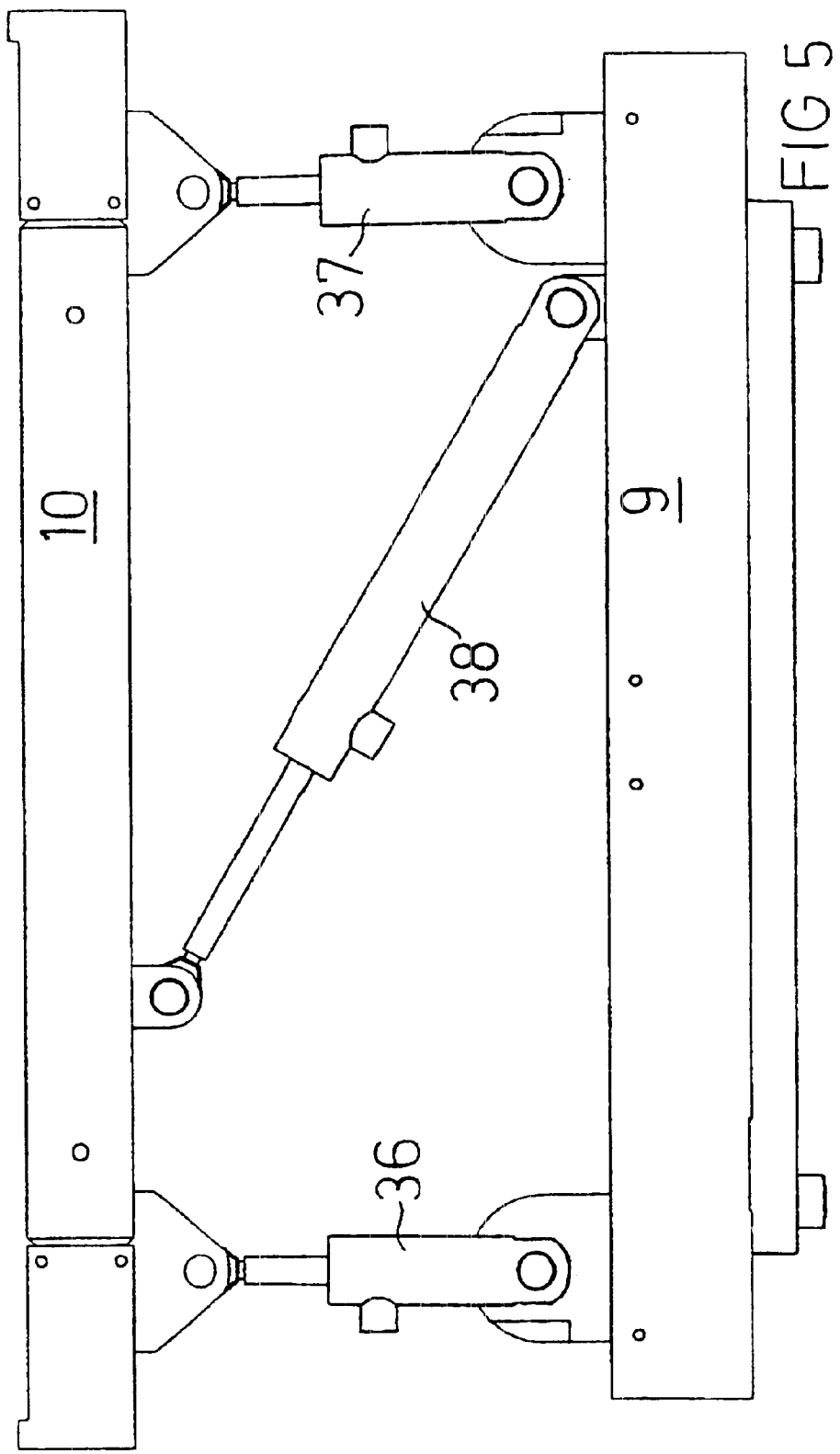
FIG. 5 shows an alternative lateral tilt mechanism.

Further, one of the tilt cylinders 13 is shown with the lower attachment point 32 on the bottom part of the elevator member 25 and with the top attachment point on the point PP on the support frame 11 at a distance from the support frame pivot point P The invention may be modified within the scope of the annexed claims. It is thus possible to use alternative lateral tilting mechanisms, such as for example traditional tilting arrangements or program controlled actuators, which may be set for traditional tilting or for tilting around an axis above the table top, see the above in detail described embodiments. In FIG. 5 the mechanism comprises two parallel actuators 36, 37 and a diagonally placed actuator 38. By appropriate control of the movement of these actuators, the frame 10 may be made to perform various chosen movements, not only movements similar to the one described with respect to the previous embodiment (FIGS. 2 and 3) but also other possibly desired movements.

Figure 6:
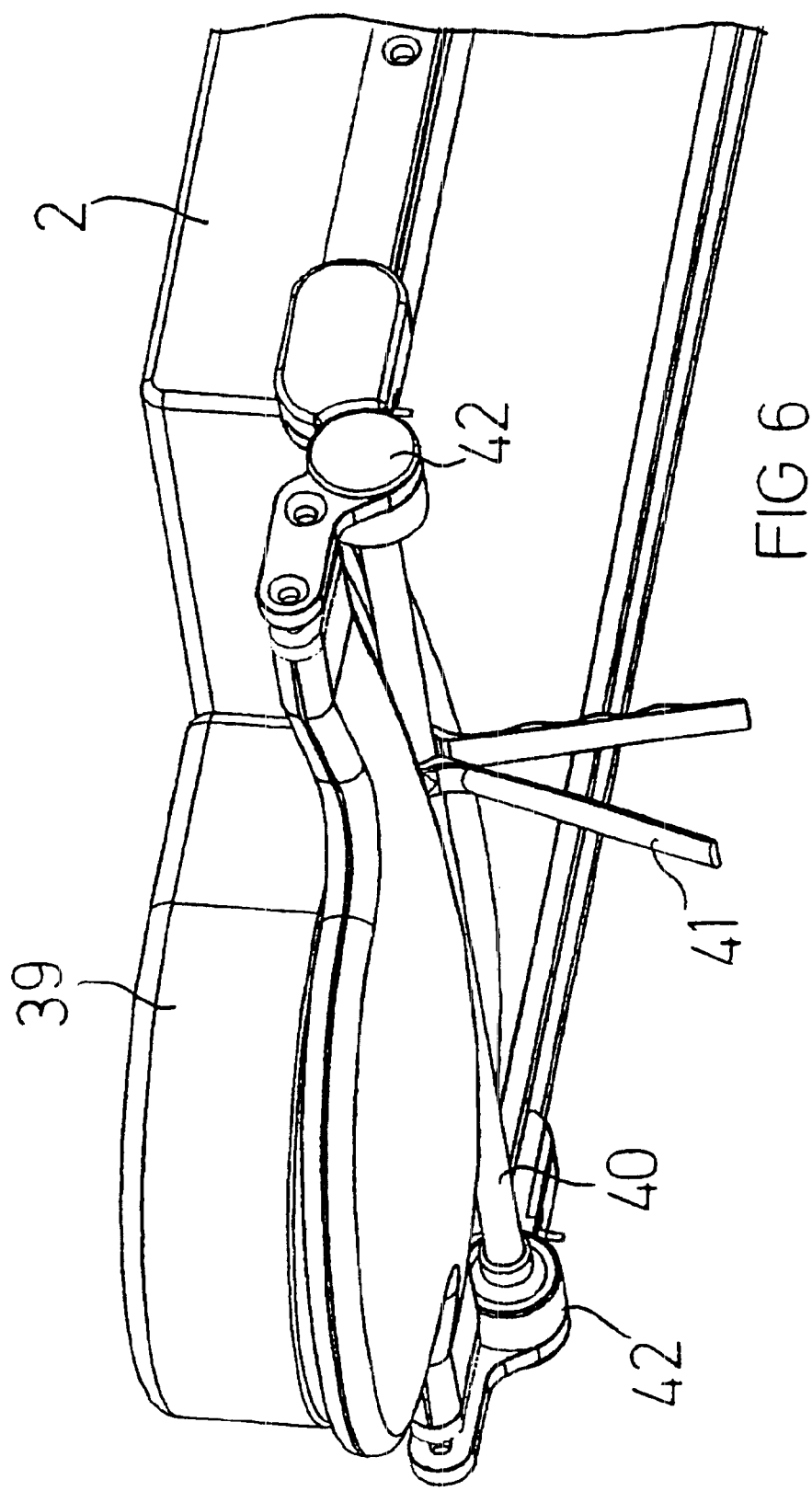
FIG. 6 shows a head support to be used with a table according to the invention.

FIG. 6 shows an adjustable head-rest 39 which is pivoted around an axis defined by the shaft 40. The head-rest 39 is on each side supported by a normally locked, overload protected rotational joint 42 which is released by turning the shaft 40 by means of the slip-grip handle 41. Turning this handle clockwise allows moving the head rest clockwise and vice versa. The device 42 may for example include a double back-stop mechanism of a per se known kind. The device 42 is easily attached to side rails equipping the table top for admitting fast and easy attachment and removal.

In order to enhance handling of the table during transport, the support structure is preferably equipped with a centrally placed guide wheel 44 (FIG. 7) which is arranged in a housing 47 and constantly in a plane substantially in parallel with the longitudinal direction of the table top. This wheel 44 is preferably placed near the centre of gravity, as seen in a view from above, and may be lowered against the floor or retracted therefrom by means of an actuator 45 operating an axis 46. When lowered, the wheel 44 acts as a directional stabiliser and helps rolling the table in desired directions also on slightly sloping surfaces and prevents undesired sideway movements of the table during transportation.

Also the longitudinal tilt mechanism may be arranged otherwise even if the mechanism described with respect to FIGS. 2 and 3 is preferred.

It is further possible to use other floating means and to use other mechanical elements than frames, although the construction with the frames is preferred because of the stability of the construction, and of the possibility to allow passage of the vertical beam which allows a vertically compact solution. In stead of frames, for example plates having essentially the same outside dimensions may be used. In this respect it is however preferred that at least the element being carried by the elevator members is a frame (in the shown embodiment the support frame 11) allowing passage of the vertical beam.

It is more preferred that also the bottom element of the lateral tilt mechanism 4 which co-operates with the support frame is also a frame (in the shown embodiment the first frame 9) allowing passage of the vertical beam.

It is most preferred that also the top element of the lateral tilt mechanism 4 is also a frame (in the shown embodiment the second frame 10) allowing passage of the vertical beam.

Other elevator mechanisms may also come into question, such as conventional telescopic elevators.

The float as well as the tilt may be program controlled, e.g. together with the vertical lift. For example it is possible to control vertical lift and longitudinal tilt so as to achieve rotation around a chosen longitudinal position of the table top. All hydraulic actuators may be replaced with mechanical ones, for example electrically driven linear actuators. The tilt may be achieved by either electrical or hydraulic power rotators co-operating with links or the like.

In the present text "comprising" is to be interpreted as "including", i.e. part of open definitions. As an example "device comprising a first element" is to be interpreted such that the device also may include second, third etc. elements.

What is claimed is:

1. A surgical table (1) comprising:
   a longitudinal, at least partly radiolucent table top (2) defining longitudinal directions and lateral directions, a support structure (3) for the table top, said support structure including a lateral tilting mechanism (4) for providing a lateral tilting movement to the table top (2) in parallel with the lateral directions, a column unit (5) for supporting the support structure and the table top, lateral floating means (6) for allowing the table top floating horizontal movement in said lateral directions relative to the column unit (5), characterized in that said lateral floating means (6) are positioned below the lateral tilting mechanism (4) permitting undisturbed lateral movement in said lateral directions in any table top position, tilted as well as horizontal.

2. The surgical table (1) according to claim 1, wherein the lateral tilting mechanism (4) is comprised of at least two longitudinally separated linkage mechanisms, each comprising two links (7), which are extending in a plane transverse to the table top (2), and which converge upwards so as to obtain lateral tilting movement of the table top (2) essentially about an axis (A) or axes being located above the table top (2).

3. The surgical table (1) according to claim 2, wherein the lateral floating means (6) is comprised of at least two parallel rails (21) and mating guides (22).

4. The surgical table (21) according to claim 1, wherein the lateral tilting mechanism (4) at the bottom is attached to a first frame (9) and at the top end to a second frame (10), each frame having longitudinal (9', 10') and transversal (9-', 10-') elements.

5. The surgical table (1) according to claim 4, wherein the transversal elements (9-') of the first frame (9) are attached to the lateral floating means (6) and the first frame (9) is thus laterally movable with respect to the base (5).

6. The surgical table (1) according to claim 4, wherein longitudinal floating means (15) are provided between the table top (2) and the second frame (10).

7. The surgical table (1) according to claim 4 wherein the first frame (9) is capable of surrounding the top portion of the beam (16) in a vertically lowest position of the table top (2) while maintaining floating and tilting capability.

8. The surgical table (1) according to claim 7, wherein the second frame (10) is capable of surrounding the top portion of the beam (16) in a vertically lowest position of the table top (2) while maintaining floating and tilting capability.

9. The surgical table (1) according to claim 1, wherein the lateral tilting mechanism (4) comprises program controlled actuators (36, 37, 38).

10. The surgical table (1) according to claim 9 wherein the actuators (4) are operative between first (9) and second (10) frames having transversal and longitudinal elements.

11. The surgical table (1) according to claim 1, wherein portions (22) of the lateral floating means (6) are attached to lateral elements (11'-) of a support frame (11) which is attached to the column unit (5).

12. The surgical table (1) according to claim 11, wherein the support frame (11) is pivotally attached (P) to a vertically displaceable elevator member (25).

13. The surgical table (1) according to claim 1 wherein longitudinal floating means (15) are provided between the table top (2) and the support structure (3).

14. The surgical table (1) according to claim 1, wherein the column unit (5) includes a table top elevator device (14, 16, 25).

15. The surgical table (1) according to claim 14, wherein the column unit (5) comprises a vertical beam (16) with vertically extending guides (17) for a vertically displaceable elevator member (25).

16. The surgical table (1) according to claim 1 wherein the floating means (6, 15) are lockable in any chosen position.

17. The surgical table (1) according to claim 1 wherein the base (5) comprises castors (19) at opposite ends thereof for movement relative to a floor, and manoeuvrable floor locks (20).

18. The surgical table (1) according to claim 17, wherein, at one end of the base (5) defined as a rear end (18), the floor locks (20) are positioned behind the rollers (19) as seen in a direction against said front end (18) so as not to obstruct movement over a door threshold or the like.

19. The surgical table (1) according to claim 1, wherein the support structure is provided with a central non-pivoting guide wheel (44), being optionally made to contact the floor and act as a directional stabiliser.

* * * * *